United States Patent
Kim et al.

(10) Patent No.: US 12,102,564 B2
(45) Date of Patent: Oct. 1, 2024

(54) OPHTHALMIC THERAPEUTIC DEVICE AND CONTROL METHOD THEREFOR

(71) Applicant: LUTRONIC CORPORATION, Goyang-si (KR)

(72) Inventors: Bong Kyun Kim, Cheonan-si (KR); Sun Jeong Ham, Seoul (KR); Gi Hoon Kim, Seoul (KR)

(73) Assignee: LUTRONIC CORPORATION, Goyang-si (KR)

( * ) Notice: Subject to any disclaimer, the term of this patent is extended or adjusted under 35 U.S.C. 154(b) by 587 days.

(21) Appl. No.: 17/416,264

(22) PCT Filed: Dec. 9, 2019

(86) PCT No.: PCT/KR2019/017316
§ 371 (c)(1),
(2) Date: Jun. 18, 2021

(87) PCT Pub. No.: WO2020/130449
PCT Pub. Date: Jun. 25, 2020

(65) Prior Publication Data
US 2022/0054307 A1    Feb. 24, 2022

(30) Foreign Application Priority Data
Dec. 18, 2018   (KR) .......................... 10-2018-0163732

(51) Int. Cl.
*A61F 9/008* (2006.01)
*G16H 20/40* (2018.01)
(Continued)

(52) U.S. Cl.
CPC ............. *A61F 9/008* (2013.01); *G16H 20/40* (2018.01); *A61B 2017/00115* (2013.01);
(Continued)

(58) Field of Classification Search
CPC ................. A61F 9/008; A61F 9/00821; A61F 2009/00851; A61F 2009/00863;
(Continued)

(56) References Cited

U.S. PATENT DOCUMENTS 6,312,422 B1 * 11/2001 Dubnack ................ B23K 26/03
                                                            351/200
2015/0190276 A1   7/2015 Ha et al.
2015/0366705 A1 * 12/2015 Ha .......................... A61F 9/008
                                                            606/6

FOREIGN PATENT DOCUMENTS

JP          2018102644 A    7/2018
KR          101015881 B1    2/2011
(Continued)

*Primary Examiner* — Scott M. Getzow

(57) ABSTRACT

The present invention relates to an ophthalmic treatment apparatus and a control method therefor, the ophthalmic treatment apparatus comprising: a display unit for displaying an image of a patient's eyeground; a treatment region setting unit for setting a treatment region on the basis of the image of the patient's eyeground; a treatment light radiating unit for radiating treatment light to the set treatment region; a radiation density setting unit for setting radiation density of the treatment light radiated to the set treatment region; and a control unit for controlling the treatment light radiating unit so as to radiate the treatment light onto the set treatment region on the basis of the set density.

19 Claims, 15 Drawing Sheets

(51) Int. Cl.
   *A61B 17/00* (2006.01)
   *A61B 18/00* (2006.01)
(52) U.S. Cl.
   CPC . *A61B 2018/00702* (2013.01); *A61F 9/00821* (2013.01); *A61F 2009/00851* (2013.01); *A61F 2009/00863* (2013.01)
(58) Field of Classification Search
   CPC .. A61F 2009/00853; A61F 2009/00891; A61F 2009/00844; G16H 20/40; G16H 30/20; G16H 30/40; G16H 40/63; A61B 2017/00115; A61B 2018/00702; A61B 3/10; A61B 3/12; A61B 90/00; A61B 3/102; A61B 90/37
   See application file for complete search history.

(56) References Cited

FOREIGN PATENT DOCUMENTS

| | | |
|---|---|---|
| KR | 20140009844 A | 1/2014 |
| KR | 101374294 B1 | 3/2014 |
| KR | 101609025 B1 | 4/2016 |
| KR | 20180012524 A | 2/2018 |

* cited by examiner

OPHTHALMIC THERAPEUTIC DEVICE AND CONTROL METHOD THEREFOR

TECHNICAL FIELD

The present disclosure relates to an ophthalmic treatment apparatus and a control method therefor and, more particularly, to an ophthalmic treatment apparatus and a control method therefor, capable of performing an optimized treatment according to a patient's lesion conditions.

BACKGROUND ART

Recently, the technology of treating a lesion by radiating beams to a body tissue and thereby changing the state of a tissue is widely applied. In particular, a laser treatment technology is widely used for various lesions related to the eyes. For example, a device for treating the lesion of an anterior eye segment, such as keratoplasty, glaucoma treatment, or cataract surgery, is widely commercialized. Recently, a device for treating a lesion occurring in an eyeground region, such as macular degeneration, is being developed. This is disclosed in Korean Patent Laid-Open Publication No. 10-2014-009844.

Such a treatment apparatus transmits energy by radiating laser to a treatment location, thereby inducing a change in the state of tissue. Even for the same lesion, the radiating distribution of a treatment beam should be set differently depending on the location or progression of a lesion. A conventional ophthalmic treatment apparatus may adjust treatment contents by adjusting the intensity of the treatment beam, but has a drawback in that distribution characteristics in which the treatment beam is radiated may not be adjusted in various ways.

DISCLOSURE

Technical Problem

The present disclosure is to provide an ophthalmic treatment apparatus and a control method therefor, capable of adjusting the radiating distribution of treatment beam in various ways in consideration of the characteristics of a patient's lesion and eyeground conditions.

Technical Solution

In order to solve the aforementioned object, the present disclosure proposes an ophthalmic treatment apparatus including a display unit for displaying an image of a patient's eyeground, a treatment region setting unit for setting a treatment region on the basis of the image of the patient's eyeground, a treatment beam radiating unit for radiating a treatment beam to the set treatment region, a radiation density setting unit for setting radiation density of the treatment beam radiated to the set treatment region, and a control unit for controlling the treatment beam radiating unit so as to radiate the treatment beam onto the set treatment region on the basis of the set density.

The set treatment region may be displayed in an overlapping manner on an eyeground image displayed on the display unit. Further, information about the set radiation density may be displayed in an overlapping manner on the eyeground image displayed on the display unit. Here, the information about the set radiation density displayed on the display unit may be displayed using at least any one of dot patterns distributed at the set density, colors, patterns, or values.

The radiation density setting unit may provide a plurality of options corresponding to various radiation densities to a user through the display unit. The plurality of options may be provided using at least one of a plurality of dot patterns distributed at different densities, a plurality of different colors, shades or patterns, and different values.

Further, the radiation density setting unit may be configured so that the user may directly input a radiation density value, and may be configured to display a distribution shape corresponding to the input radiation density value to the user.

In another embodiment, the display unit may be configured to display an eyeground sample chart in which main organs of the eyeground are schematically displayed so as to set the treatment region, and the treatment region setting unit may be configured to set the treatment region on the eyeground sample chart.

The display unit may be configured to display an eyeground sample chart in which main organs of the eyeground are schematically illustrated so as to set the radiation density of the treatment beam and the set treatment region is displayed, and the radiation density setting unit may be configured to display the information about the set radiation density in the treatment region displayed on the eyeground sample chart.

The treatment region setting unit may be configured to set the set treatment region into a plurality of sub-regions according to a patient's eyeground condition, and the radiation density setting unit may set the radiation density of the treatment beam for each of the plurality of sub-regions.

The treatment beam radiating unit may be operated to randomly radiate the treatment beam to the set treatment region at the set radiation density.

Furthermore, the present disclosure proposes a method of controlling an ophthalmic treatment apparatus including displaying an eyeground image on a display unit, setting a treatment region in which treatment is performed, on the basis of the eyeground image; setting radiation density of treatment beam radiated to the treatment region, and radiating the treatment beam to the set treatment region at the set radiation density.

In the setting the treatment region, a boundary of the treatment region may be displayed on the eyeground image displayed on the display unit to set the treatment region, and the display unit may display the set treatment region on the eyeground image in an overlapping manner.

In the setting the radiation density, a plurality of options corresponding to various radiation densities may be displayed through the display unit, and a user may set the radiation density by selecting one of the plurality of options, or the user may directly input a radiation density value. Further, the information about the set radiation density may be displayed inside the treatment region displayed on the eyeground image in an overlapping manner.

In the setting the treatment region, an eyeground sample chart in which main organs of the eyeground are schematically displayed may be displayed through the display unit, and the user may set the treatment region on the eyeground sample chart.

Moreover, in the setting the radiation density, an eyeground sample chart in which main organs of the eyeground are schematically illustrated and the set treatment region is displayed may be displayed through the display unit, and the information about the set radiation density may be displayed in the treatment region displayed on the eyeground sample chart.

Moreover, the setting the treatment region may further include partitioning the set treatment region into a plurality of sub-regions according to a patient's eyeground condition, and in the setting the radiation density, the radiation density of the treatment beam may be configured to be set for each of the partitioned sub-regions.

Advantageous Effects

According to the present invention, a treatment is performed after radiation density of radiated treatment beam is adjusted according to a patient's lesion condition and lesion location, so that the treatment can be optimally performed.

In addition, an interface enabling a user to easily adjust and set a treatment location and radiation density of treatment beam is provided, so that operability of the user can be improved.

MODE FOR DISCLOSURE

Hereinafter, an ophthalmic treatment apparatus and a control method therefor in accordance with an embodiment of the present disclosure will be described in detail with reference to the accompanying drawings. In the following description, the positional relationship between respective components will be described with reference to the drawings in principle. The drawings may be shown by simplifying the structure of the disclosure for the convenience of description or exaggerating if necessary. However, the present disclosure is not limited thereto. In addition, various devices may be added, changed or omitted.

As the ophthalmic treatment apparatus that will be described below, a device for treating an eyeground lesion will be mainly described. However, the present disclosure may also be applied to a treatment device for treating the eyeground lesion as well as other ophthalmic lesions. For example, the present disclosure may be applied to a device for treating the lesion of the anterior eye segment, such as glaucoma, and be applied to a device for treating the lesion occurring in a crystalline lens, such as cataract. Moreover, it should be noted that the present disclosure may be widely used in a treatment device for treating lesions of other medical branches, such as a skin lesion, as well as the ophthalmic lesion.

Hereinafter, the term 'treatment region' is a region in which treatment is required to treat, a lesion, and may refer to a region having a predetermined area or a predetermined length. Furthermore, the term 'treatment location' may refer to a location where treatment is performed in the treatment region. Moreover, the term 'target tissue' may refer to a tissue that is to be treated.

In other words, if a beam is radiated to the specific 'treatment location' in the shape of a spot, most of energy may be transmitted to the 'target tissue' located at a specific depth of the corresponding treatment location. Furthermore, in order to treat the 'treatment region' of the predetermined area, treatment may be performed by sequentially radiating beams to a plurality of 'treatment locations' located in the treatment region.

Figure 1:
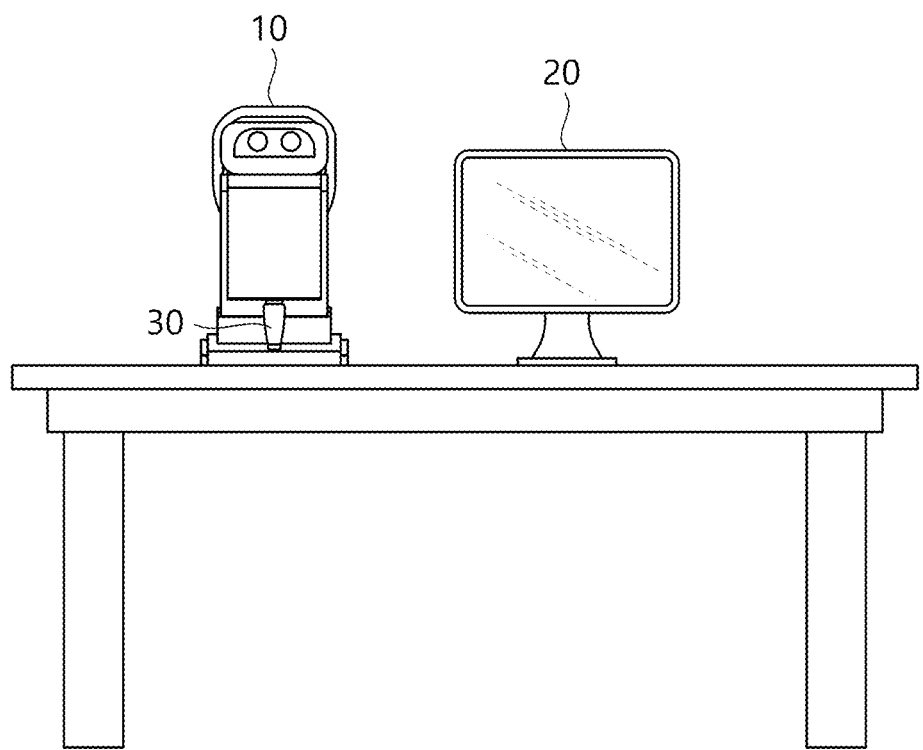
FIG. 1 is a diagram illustrating the configuration of an ophthalmic treatment apparatus in accordance with an embodiment of the present disclosure.

FIG. 1 is a diagram schematically illustrating the configuration of an ophthalmic treatment apparatus in accordance with an embodiment of the present disclosure. The ophthalmic treatment apparatus in accordance with this embodiment is a device for performing treatment by radiating a treatment beam to the eyeground, and includes a main body 10 and an interface unit 20 as illustrated in FIG. 1.

The main body 10 is a device with which a user performs treatment while observing a patient's eye. An object part 170 is provided on a side of the main body 10 to fix the location of the patient's eye. Various components that will be described below in detail may be provided in the main body to perform treatment. The main body may have a slit lamp structure equipped with an eyepiece part for observing the patient's eye, or may be configured such that a separate eyepiece part is not provided in the main body and a user observes the patient's eye using an image displayed through the interface unit. An operation unit 30 may be provided on an outside of the main body to control the operation of the treatment apparatus. The operation unit 30 may be configured using a structure such as a keyboard, a joystick, or a pedal, and a user may operate the operation unit to control an observing direction, the operation of the treatment apparatus, etc.

The interface unit 20 is provided at a location adjacent to the main body 10. The interface unit may be configured to display various pieces of information required for a user during treatment, or be configured such that a user inputs information or sets treatment contents through the interface unit.

Figure 2:
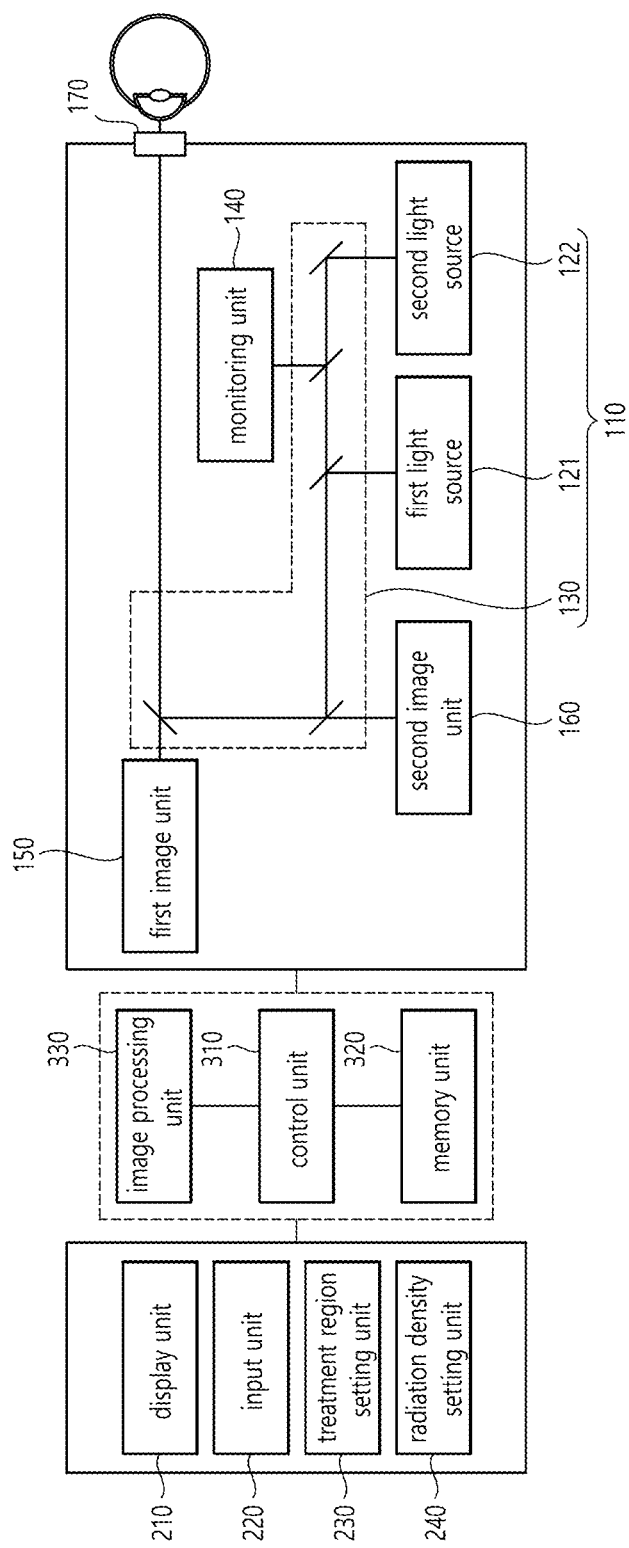
FIG. 2 is a diagram illustrating main components of the ophthalmic treatment apparatus of FIG. 1.

FIG. 2 is a block diagram schematically illustrating main components of the ophthalmic treatment apparatus of FIG. 1. The main body 10 includes a treatment beam radiating unit 110 that generates a treatment beam to radiate the treatment beam to an eyeground. The treatment beam radiating unit 110 includes at least one light source 121 or 122 that generates a treatment beam and a beam delivery unit 130 that delivers the treatment beam generated by each light source to the eyeground. This may further include an aiming beam generating unit (not shown) to indicate a location to which the treatment beam is radiated. Moreover, the treatment apparatus may further include a monitoring unit 140 for sensing a change in the suite of tissue by the treatment beam during treatment, and at least one image unit 150 or 160 for acquiring information about the image of a patient's eyeground.

The treatment beam radiating unit 110 according to this embodiment includes the first light source 121 and the second light source 122. The first light source 121 and the second light source 122 may be configured to generate treatment beams of different wavelengths, and may be used for different lesions or for different treatment purposes. The first light source 121 and the second light source 122 may be individually operated, and various parameters such as the radiation and stop of the treatment beam, the intensity of the treatment beam, and the pulse width of the treatment beam may be controlled by the control unit 310.

First, the first light source 121 generates a treatment beam for performing retinal photocoagulation treatment on the eyeground. The treatment beam generated by the first light source 121 transmits relatively higher energy to the tissue as compared to that of the treatment beam generated by the second light source 122. Therefore, this causes the thermal denaturation of the tissue, thus leading to photocoagulation. The first light source 121 may be controlled to be radiated with various sprit sizes to the lesion of the eyeground, and may treat various lesions of the eyeground. The first light source 121 of this embodiment may be configured to generate the treatment beam having the wavelength of 577 nm, and may include an optical element such as a variable field stop and a collimator.

Further, the second light source 122 generates the treatment beam to perform selective retina therapy on the eyeground. The selective retina therapy is a therapy method that induces a change in the slate of target tissue by radiating the treatment beam of relatively low energy as compared to the aforementioned retinal coagulation. Generally, in the retinal coagulation, the treatment beam is radiated to a level where the tissue is photocoagulated and albinism is observed. On the other hand, the selective retina therapy is a therapy method where energy is selectively transmitted to only target tissue located inside the tissue without damaging optic nerves, thus causing a change in the state of the target tissue. Therefore, the second light source 122 allows precise treatment to be performed with treatment beam having relatively low energy. The second light source 122 may include a laser medium or a laser diode such as Nd:YLF, Nd:YAG, Ho:YAG. In this embodiment, the second light source is configured to radiate the treatment beam having the wavelength of 527 nm. This may further include an optical element such as a variable field stop and a collimator. A therapy method using the second light source will be described below in detail.

The beam delivery unit 130 is composed of a plurality of optical elements to form an optical path along which the treatment beam travels. Therefore, the treatment beam radiated by each light source is radiated through the beam delivery unit 130 to the patient's eyeground. Such a beam delivery unit 130 includes a scanner to adjust a location where the treatment beam is radiated, in addition, the beam delivery unit may include a plurality of optical elements such as an optical lens, a filter, or a shutter to adjust various parameters including the spot size of the treatment beam. Moreover, the beam delivery unit 130 may include a plurality of beam combiners to form an optical path along which an image beam, an aiming beam, or a detection beam as well as the treatment beam travels. Although FIG. 2 shows the schematic structure of the beam delivery unit, the present disclosure may be changed in various ways without being limited thereto.

An object part 170 is provided on an end of the beam delivery unit. The object part 170 is a part at which a patient's eye to be treated is located, and may include an object lens or a contact lens coming into contact with the patient's eye.

Meanwhile, the aiming beam generation unit (not shown) generates the aiming beam. The aiming beam is radiated to a location where the treatment beam is radiated to confirm the location where the treatment beam is radiated before the treatment beam is radiated or while the treatment beam is radiated, thus providing the associated location to a user. When the radiated aiming beam is reflected by the eyeground to be transmitted through the beam delivery unit 130 to the eyepiece part where the user's eye is located, this is displayed on the photographed eyeground image, thus allowing the user to confirm the location through the interface unit. However, when a coordinate value associated with the radiation of the treatment beam is displayed through the interface unit as the treatment location, the aiming beam generating unit may be omitted.

The monitoring unit 140 is configured to monitor the treatment for the treatment location by the treatment beam during treatment. Such a monitoring unit 140 may use at least one of various devices an optoacoustic sensor, a reflectometry sensor, a temperature sensor, an optical detector, and an ultrasonic sensor. Further, while the treatment beam is radiated to the treatment location, it is possible to detect information about a change in the state of the treatment location in real time, and thereby determine whether the change in the state has reached a target level.

The monitoring unit 140 of this embodiment may be the reflectometry sensor. The monitoring unit may receive the beam reflected from the treatment location during the treatment, analyze the parameter of the received beam, and monitor the state information about the treatment location. Here, the monitoring unit 140 may receive the reflected treatment beam to perform a monitoring operation. However, the monitoring unit 140 of this embodiment may be provided with a separate detection-beam source to radiate a detection beam to the treatment location during the treatment, analyze the reflected detection beam, and thereby monitor a change in the state of the treatment location. The monitored result may be provided to a user through the display unit 210, and the control unit 310 may be configured to automatically control the treatment contents on the basis of the monitored information in real time.

Meanwhile, the image units 150 and 160 are configured to obtain the image of the patient's eyeground. The image units of this embodiment include a first image unit 150 configured to obtain a two-dimensional image of the eyeground, and a second image unit 160 configured to obtain a tomographic image of the patient's treatment region.

The first image unit 150 includes an image light source and an image capturing element. An image beam radiated from the image light source may be radiated to the surface of the eyeground, and the image beam reflected from the surface of the eyeground may be transmitted to the image capturing element, thus acquiring the eyeground image. The first image unit 150 may obtain a two-dimensional image for the surface of the retina (surface in the direction of the center of the eyeball), and may obtain the image of tissue located inside the surface of the retina by a predetermined thickness according to the wavelength of the image beam.

The first image unit 150 according to this embodiment includes a first image light source (not shown) that radiates beam having the wavelength of a visible-ray band and a second image light source (not shown) that radiates beam having the wavelength of an infrared band, thus selectively obtaining a visible-ray eyeground image and an infrared eyeground image. Since the visible-ray eyeground image obtained by the first image light source has a relatively high resolution, it is photographed before or after treatment and is used to check the condition of the patient's eyeground, a lesion location, and a treatment result. On the other hand, since the second image light source radiating infrared rays may obtain an image in a state where a patient's visual stimulation is minimized, it is used to check the eyeground image in real time during treatment.

The second image unit 160 is configured to acquire the tomographic image of the patient's eyeground, and is configured with an eyeground OCT device using an optical interference phenomenon. The information obtained by the second image unit 160 to generate the tomographic image includes various pieces of tomographic information about the eyeground. For example, various pieces of tomographic information may be included, such as information about the thickness of the retina, information about the thickness of each tissue layer forming the retina, the location in a depth direction and the shape of a new blood vessel, or the location in a depth direction and the shape of a byproduct such as drusen. Therefore, the second image unit 160 may not only generate the tomographic image of the treatment region but also may serve as a tomographic-information acquirer for acquiring the tomographic information about the treatment region. Such a second image unit may be formed using various OCT devices, which are well known to those skilled in the art, such as an SS-OCT or an SD-OCT.

Meanwhile, as shown in FIG. 2, the interface unit 20 includes a display unit 210, an input unit 220, a treatment region setting unit 230, and a radiation density setting unit 240. Here, the display unit 210 is configured to display and transmit various pieces of information to a user, and the input unit 220 is configured to allow a user to input various pieces of information or setting contents. The treatment region setting unit 230 is configured to set a treatment region of a patient's eyeground which is to be treated, and the radiation density setting unit 240 is configured to set the radiation density of the treatment beam radiated to the treatment region.

First, the display unit 210 is formed of a display device that may display various pieces of information including images photographed by the main body. The eyeground image (including the visible-ray eyeground image and the infrared eyeground image) acquired by the above-described first image unit 150, the eyeground tomographic image acquired by the second image unit 160, or various images acquired by a separate diagnostic device are displayed on the display unit 210. In addition, the display unit 210 displays various pieces of information such as patient information, treatment options provided by the device, or information obtained by the monitoring unit. The user may check various pieces of information including the above-described image through the display unit 210.

The input unit 220 is configured such that the user inputs various pieces of information and setting contents into the treatment apparatus. The user selects and inputs the patient information, or performs various input operations including an operation of setting treatment information, through the input unit 220. When the display unit 210 is formed of a display device having a touch screen function, the input unit 220 may be formed of a module integral with the display unit 210 to perform an input operation through a screen touch. Alternatively, the input unit may be formed using a keyboard, a mouse, or an input pen.

As described above, the treatment region setting unit 230 is configured to set the treatment region A. The treatment region may be set in such a way that the user directly sets the treatment region with reference to the eyeground image. In this case, the user sets the boundary of the treatment region on the eyeground image displayed on the display unit 210 using the finger or the input pen, or sets the boundary using a device such as a separate mouse. In FIG. 2, the treatment region setting unit 230 and the input unit 220 are configured as separate blocks. However, it is to be understood that the treatment region setting unit 230 may be included in the input unit 220, because the treatment region setting unit may also perform an input operation. However, according to another embodiment, the treatment region setting unit 230 may be configured to process the eyeground image acquired by the first image unit 150 and thereby automatically set the treatment region without a separate user input (e.g., automatically set the treatment region on the basis of the contrast information of the eyeground image).

The radiation density setting unit 240 is configured to set the radiation density of the treatment beam radiated to the treatment region. Here, the radiation density may mean the number of treatment beams radiated per unit area, and may mean the number of treatment beams radiated into the treatment region. The user may adjust the radiation density in the treatment region depending on the contents of the lesion, the progress of the lesion, the location where the lesion occurs, and the condition of the patient's eyeground tissue. For example, in the case of an initial lesion, the treatment beam may be radiated at a low density. When the lesion has progressed considerably, the treatment beam may be radiated at a high density. Alternatively, at a dangerous location where the optic nerves are relatively dense, the treatment beam may be radiated at a low density. At a relatively safe location, the treatment beam may be radiated at a high density. Thus, the user sets a proper radiation density through the radiation density-setting unit 240 according to judgment, and the control unit 310 radiates the treatment beam to have a distribution corresponding to the treatment region on the basis of the set radiation density. The radiation density setting unit 240 may be formed in the interface unit 20 through various methods. For example, the radiation density may be set using a touch screen method through a setting window provided through the display unit or a separate mouse device. In FIG. 2, the input unit 220 and the radiation density setting unit 240 are configured as separate blocks. Although they are separately illustrated to describe a function and a purpose, it is to be understood that the radiation density setting unit may be included in the input unit.

Meanwhile, the control unit 310 is configured to control the operation of the main components of the main body including the treatment beam radiating unit 110, the image units 150 and 160, and the monitoring unit 140. The control unit 310 controls the components on the basis of a self-control algorithm stored in the memory unit 320, contents where the user operates through the operation unit 30, or contents that are input or set through the interface unit 20. Further, the control unit serves to process and operate the information monitored by the monitoring unit 140 and then transmit the information to another component.

The memory unit 320 is configured to store various pieces of information and algorithms related to the operation of the components, and to store the information monitored by the first and second image units or the monitoring unit. Further, the image processing unit 330 is configured to process the information acquired by the first image unit and the second image unit in a form that may be displayed on the display unit 210, or to convert associated images or convert the set information on the image.

Although FIG. 2 illustrates that the control unit 310, the memory unit 320, and the image processing unit 330 are blocks separate from the main body 10 and the interface unit 20, they may be installed on one side or both sides of the main body or the interface unit without being limited to the above-described installation locations.

Figure 3:
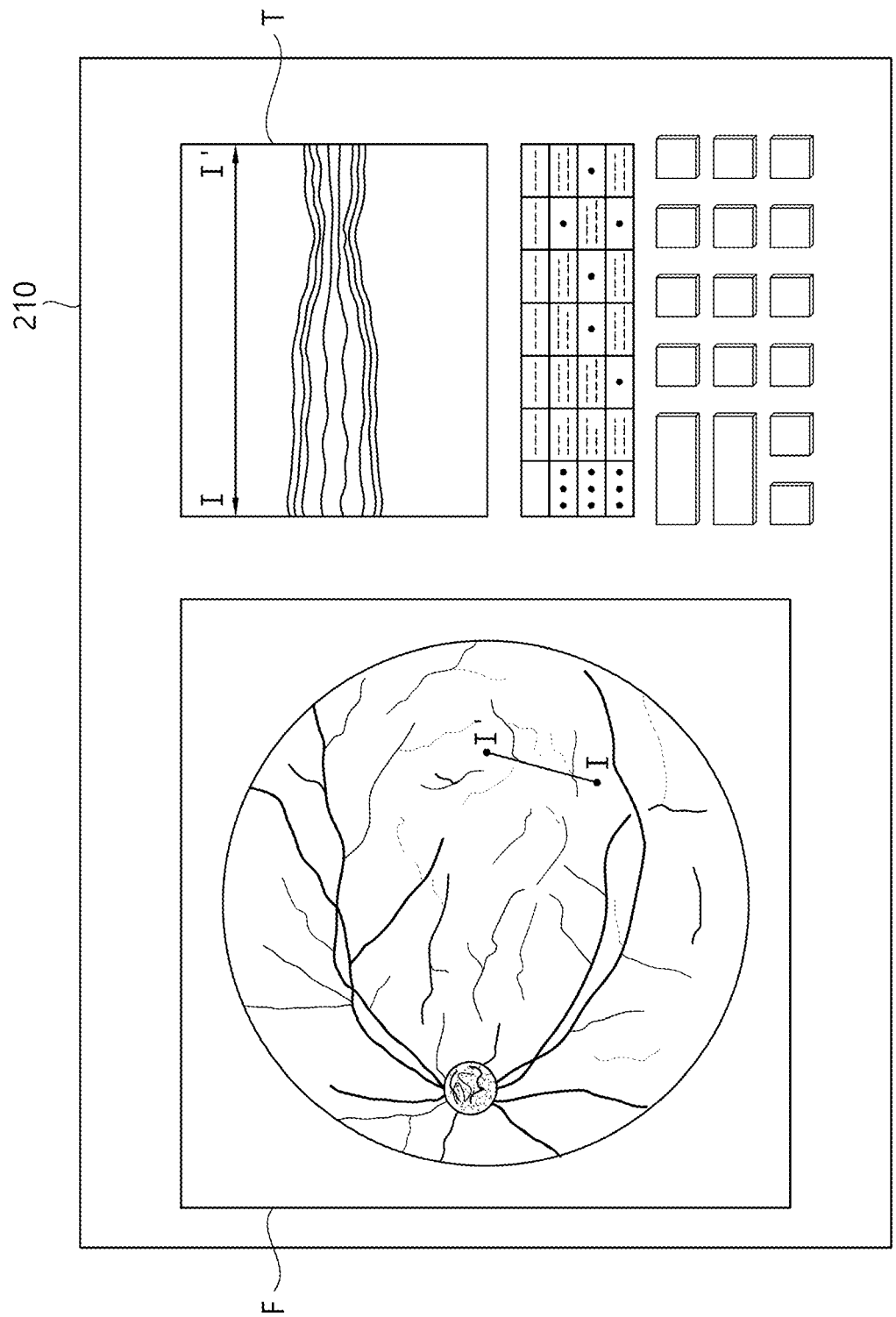
FIG. 3 is a diagram illustrating an image displayed on a display unit of FIG. 2.

FIG. 3 is a diagram illustrating an image displayed on the display unit of FIG. 2. As shown in FIG. 3, the eyeground image P obtained from the first image unit 150 may be displayed on a portion of the display unit 210, and the tomographic image T of the eyeground obtained from the second image unit 160 may be displayed on another portion thereof. Further, an option and input window for various pieces of information and user input or setting may be displayed.

The eyeground image F of FIG. 3 may be a visible-ray eyeground image photographed using the first image light source of the first image unit 150. The user may check the condition of the patient's lesion before treatment based on the visible-ray eyeground image F displayed on the display unit 210 and then set the treatment location. Alternatively, the eyeground image F of FIG. 3 may be an infrared eyeground image photographed using the second image light source, may be photographed in real time during treatment and then be displayed to allow the user to check a treatment situation. Furthermore, according to another embodiment, the tomographic information of the eyeground obtained by the second image unit may be processed, and the tomographic information for each eyeground location may be displayed on the eyeground image in an overlapping manner.

The eyeground tomographic image T of FIG. 3 may be a tomographic image at a location selected by the user. When the second image unit 160 obtains the tomographic information about various locations of the eyeground, and the user selects a specific location (e.g., line I-I' of FIG. 3) on the eyeground image F, the tomographic image T of a corresponding location may be generated and be displayed on the display unit. The user may confirm, through the displayed eyeground tomographic image T, information such as the shape and thickness of a multilayered structure of the retina at a corresponding location, the generation of a blood vessel, or the generation of drusen.

Figure 4:
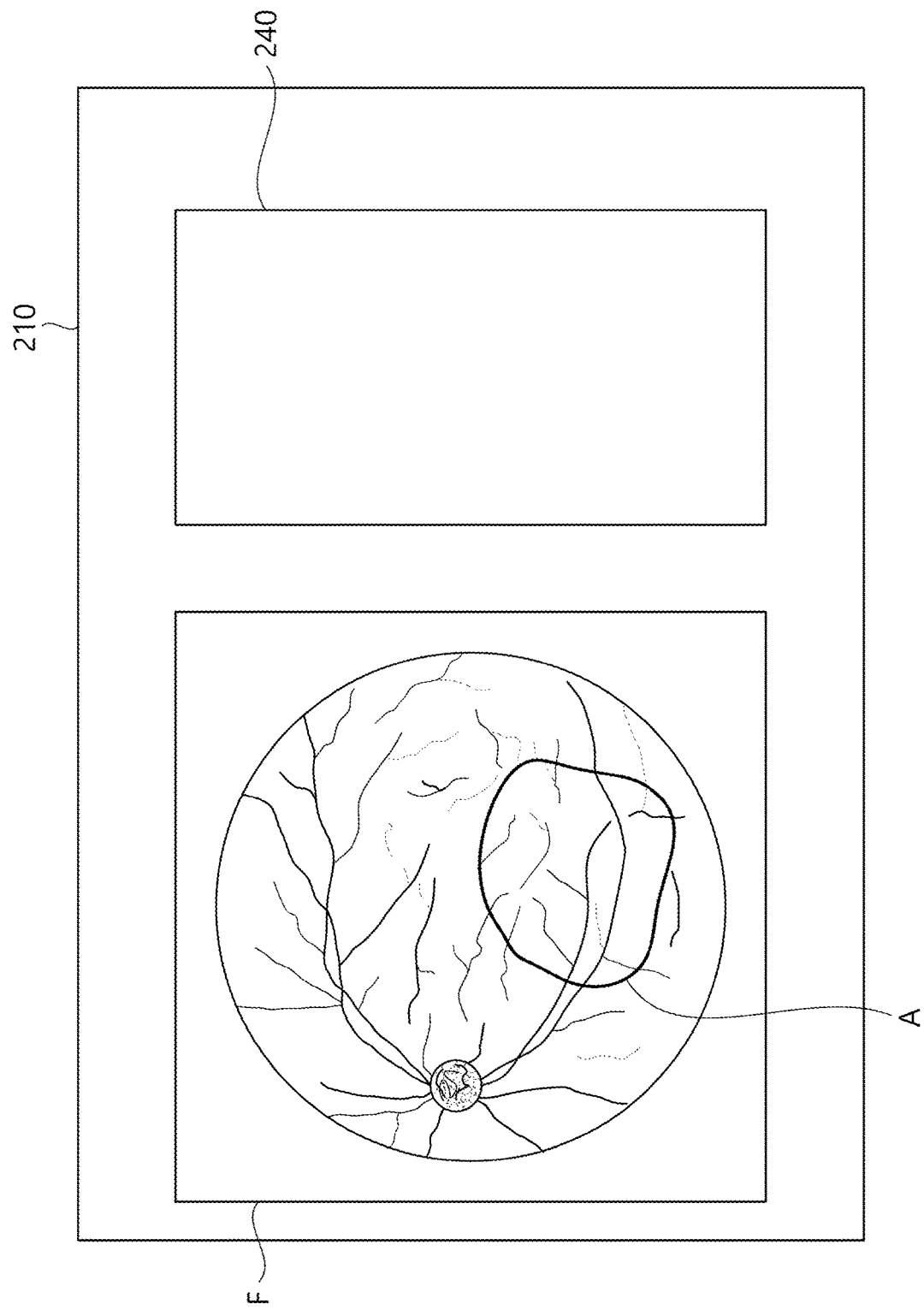
FIG. 4 is a diagram illustrating an image of the display unit for setting a treatment region and radiation density.

FIG. 4 is a diagram illustrating the image of the display unit for setting the treatment region and the radiation density. The user sets the treatment region based on the eyeground image and the eyeground tomographic image of FIG. 3. As described above, the treatment region may be set using the treatment region setting unit 230. According to this embodiment, this may be done by setting the boundary of the treatment region A using the touch screen function or a separate input device on the eyeground image F displayed on the display unit 210. The set treatment region A may be displayed on the eyeground image of the display unit in an overlapping manner. If the treatment region A is set, the user sets the treatment contents, which are to be performed in the treatment region, through the display unit. To this end, the user sets the radiation density of the treatment beam radiated to the treatment region, and such an operation is performed through the radiation density setting unit 240 shown on a side of the display unit 210. The radiation density setting unit may be formed in various ways, and specific examples thereof will be described below. Thus, if the treatment region and the radiation density are set through the interface unit 20, the control unit 310 operates the treatment beam radiating unit 110 to radiate the treatment beam to the set treatment location and thereby perform the treatment.

First, in the case of performing the treatment through the retinal photocoagulation method, the control unit 310 controls the first light source 121 to perform the treatment. Here, the treatment beam is radiated with a preset pulse width and a preset output, thus allowing the same level of energy to be transmitted to respective treatment locations. The treatment beam radiated to one location may be formed of a single pulse or a plurality of pulses having the same intensity. As described above, the treatment beam radiated from the first light source 121 transmits relatively high energy to the treatment location, thus inducing the photocoagulation in the tissue of the treatment location.

The treatment by the first light source 121 is performed as follows. As shown in FIG. 4, if the treatment region and the treatment location are determined, and the user inputs an operation command once, a control may be performed such that treatment beams are sequentially radiated to a plurality of treatment locations. However, as described above, since the treatment beam generated by the first light source 121 is radiated to the treatment location with a relatively wide spot size, the control may be performed such that the user selects a required lesion location to radiate the treatment beam thereto without performing the step of setting a separate treatment region.

Figure 5:
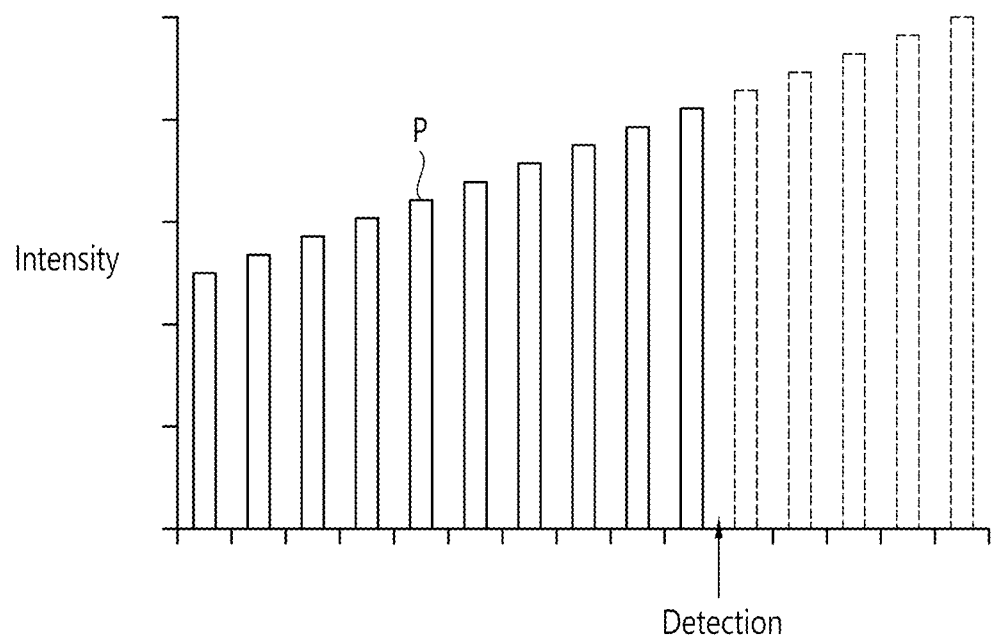
FIG. 5 is a graph illustrating an example of a treatment beam radiated from a second light source to one treatment location.

Meanwhile, in the case of performing the selective retina therapy, the control unit 310 controls the second light source 122 to perform the treatment. FIG. 5 is a graph illustrating an example of the treatment beam radiated from the second light source 122 to one treatment location. As shown in FIG. 5, the second light source 122 radiates the treatment beam in the form of a pulse train composed of a plurality of micropulses P, the intensities of which are sequentially increased, to one treatment location.

The selective retina therapy using the second light source 122 selectively transmits energy to a RPE cell layer that is the target tissue located inside the retina in the retina tissue having a multilayered structure. This uses the wavelength characteristics of the treatment beam that is rarely absorbed by a cell layer (optic-nerve layer) located in front of the retina and is selectively absorbed by the melanosome of the RPE cell layer. If energy is absorbed by the melanosome, the temperature of the RPE cell increases. If the absorbed energy exceeds a predetermined level, the RPE cell reaches a targeted change in state and is replaced with a healthy cell. Here, the targeted state change is a state where the temperature of the RPE cell increases and a preset level of microbubbles is generated and grown on a surface of the melanosome. In this case, it is determined that a corresponding RPE cell selectively necroses, thus inducing a new RPE cell.

Since energy absorbed by the melanosome is dispersed within a short period of time, it is possible to reach a targeted state change only when the intensity of the pulse of the radiated treatment beam exceeds a predetermined level. On the other hand, when the intensity of the pulse of the treatment beam is too high, the RPE cell as well as an adjacent photoreceptor may be damaged, thus causing damage to eyesight. Therefore, according to the present disclosure, in order to perform the treatment with an optimum intensity, the treatment beam in the form of a pulse train whose intensity is sequentially increased is radiated to one treatment location, thus performing treatment. If the targeted state change is detected at a corresponding treatment location during the treatment, a control may be performed to stop radiating the treatment beam.

To be more specific, in this embodiment, the treatment beam radiated to one treatment location is composed of 15 micropulses P. Here, each micropulse P may be radiated at the period of about 20 to 200 Hz, and the pulse width of each micropulse may range from 1 to 5 µs. The intensity of an initial micropulse may correspond to 50% of the intensity of a fifteenth micropulse, and each micropulse may be formed evenly to increase by about 3.57% of the intensity of the fifteenth micropulse. Here, by the user's setting or the control of the control unit, parameters such as the intensity of the initial micropulse and a gap at which the intensity of the micropulse increases may be adjusted.

While a plurality of micropulses is radiated to one treatment location, the monitoring unit 140 monitors a change in the state of the treatment location. If the targeted state change is detected in the target tissue through the monitoring unit 140 (the detection of a change in scattering pattern caused by the microbubble generation and a change in various signals including a sound wave signal) during the radiation, the radiation of the treatment beam is completed at a corresponding location without radiating the remaining micropulses. FIG. 5 shows that a targeted state change is detected in a state where a tenth micropulse is radiated, so that 10 micropulses are radiated and the treatment of a corresponding location is completed.

As shown in FIG. 4, if the treatment region and the treatment location are determined, the control unit 310 controls to sequentially treat a plurality of treatment locations in response to the user's operation command. At this time, a plurality of micropulses is radiated to each treatment location in the above-described manner. Since time when the treatment is completed at a corresponding location is determined under a feedback control according to a monitored result, the number of micropulses radiated to each treatment location may be different. In other words, since the treatment is performed by transmitting the energy of a required level depending on the tissue characteristics of each treatment location, the treatment may be performed while minimizing damage to adjacent tissue.

FIGS. 6 to 9 are diagrams illustrating an example of the radiation density setting unit of FIG. 4. Hereinafter, various examples of the radiation density setting unit 240 will be described in detail with reference to FIGS. 6 to 9.

As shown in FIG. 4, the radiation density setting unit 240 is displayed on one side of the display unit, and provides a plurality of options corresponding to various radiation densities through the display unit 210 to the user. The user selects a desired radiation density option among various options, thus setting the radiation density.

Figure 6:
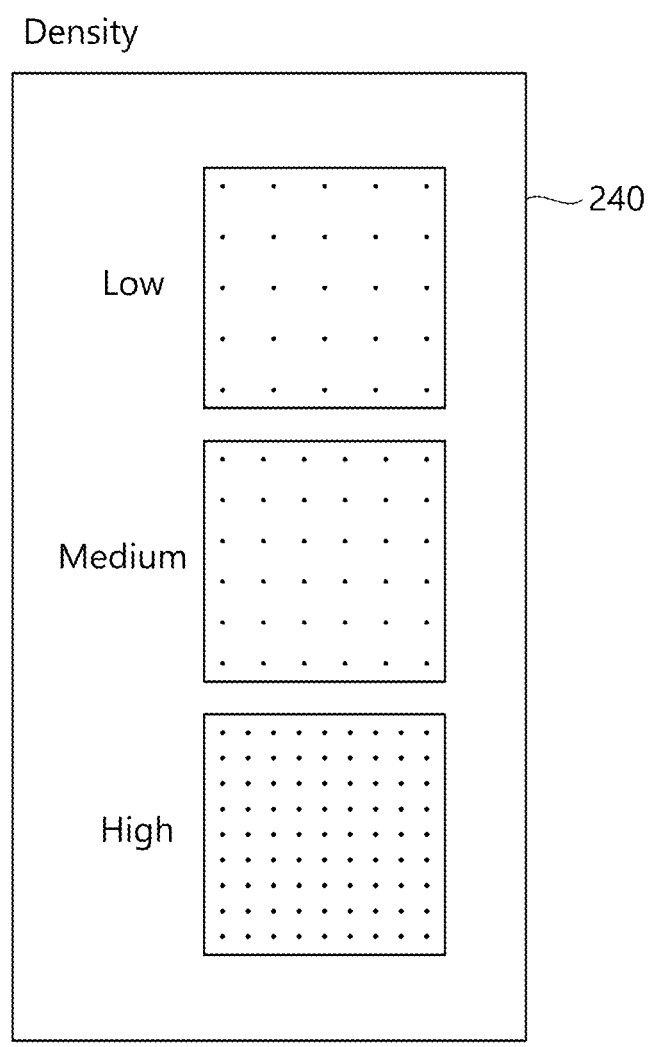
FIGS. 6 to 9 are diagrams illustrating an example of a radiation density setting unit of FIG. 4.

As one example, as shown in FIG. 6, the radiation density setting unit 240 may provide a plurality of dot patterns distributed at different densities as an option. The user may select one of a low radiation density, a medium radiation density, and a high radiation density depending on the compactness of the dot pattern. When the dot pattern is used, there is an advantage that distribution where the treatment beams are radiated can be intuitively predicted. Although FIG. 6 shows only three options, this is merely illustrative. It is possible to provide more options having a different compactness or a different distribution shape.

Figure 7:
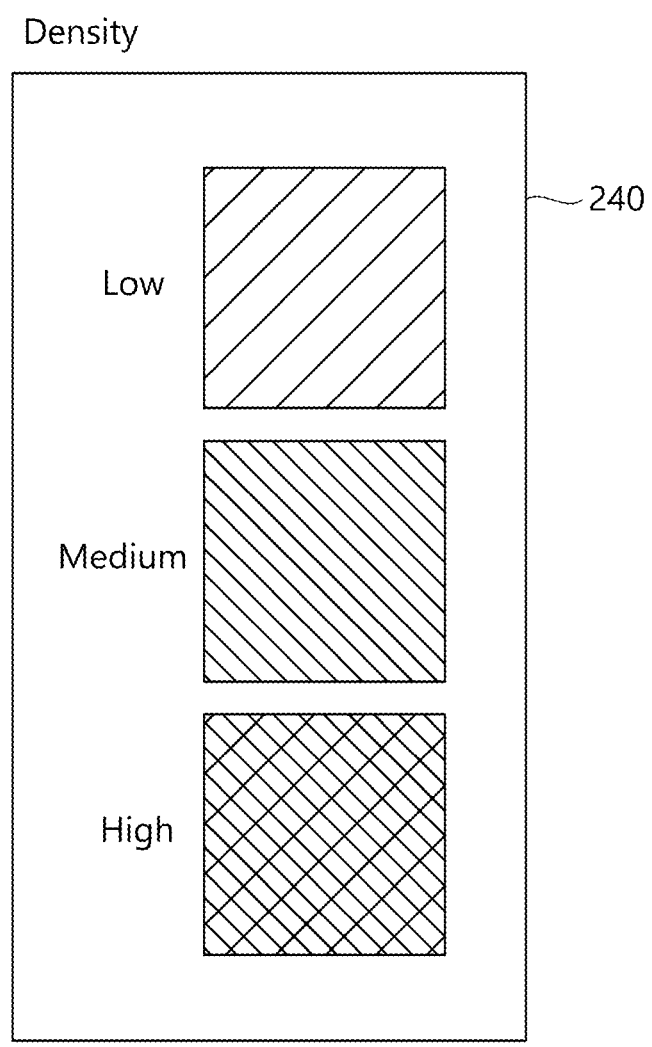

As another example, as shown in FIG. 7, the radiation density setting unit 240 may provide different patterns as an option. The respective patterns correspond to different radiation density values, and the user selects an option corresponding to a desired radiation density among a plurality of patterns to set the radiation density. According to this embodiment, the set radiation density can be more clearly identified when the radiation density information is displayed on the eyeground image in an overlapping manner, as compared to the embodiment of FIG. 6. Although FIG. 7 shows an option using a pattern, it is possible to provide radiation density options using different colors or shades. Alternatively, as shown in FIG. 8, the radiation density setting unit may provide different values as an option.

Figure 8:
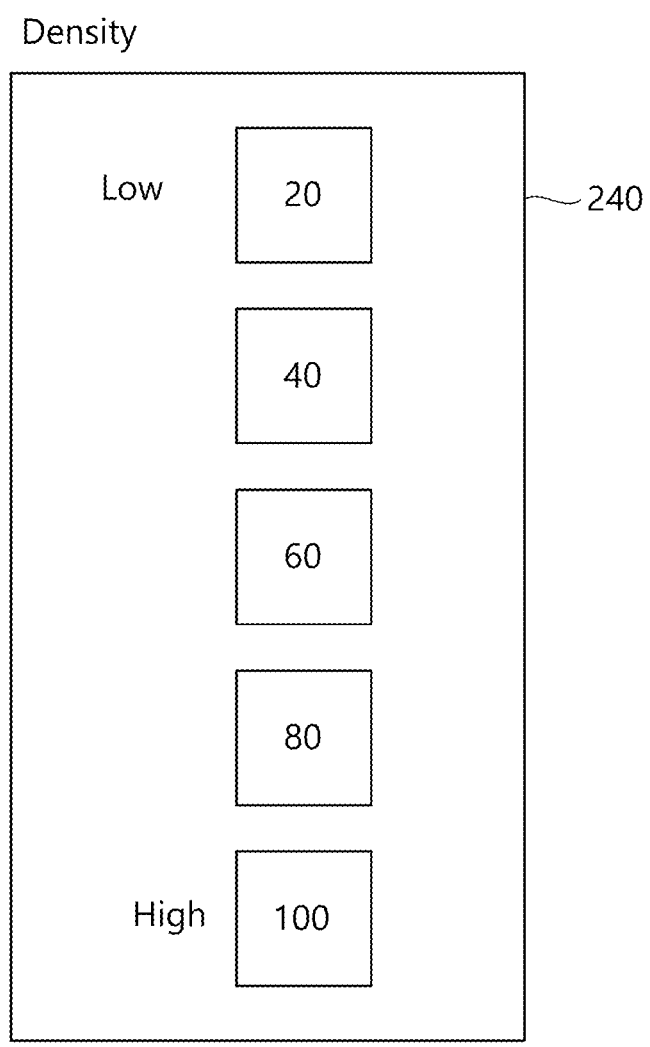
Figure 9:
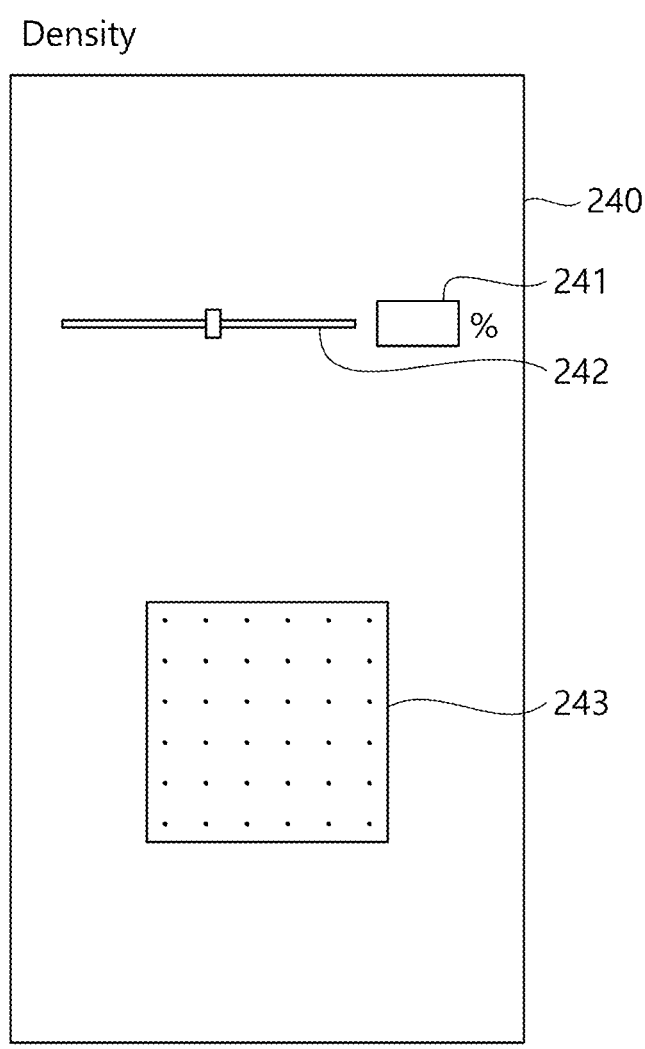

Meanwhile, an example of FIGS. 6 to 8 may be configured so that the user directly inputs and sets a radiation density value, as compared to an example where the user selects several options. As shown in FIG. 9, the radiation density setting unit 240 includes an input window 241 to allow the user to input a value, so that the user may input and set a desired distribution value. Moreover, a bar-shaped range slider 242 is provided, so that the user may set the radiation density value while moving the slider. In this case, it is possible to set the optimum radiation density while linearly adjusting the radiation density value.

A region 243 may be provided under the input window 241 and the range slider 242 to schematically indicate a radiation density corresponding to a selected radiation density. Therefore, the user may set the radiation density value based on the distribution shape of spots displayed in the corresponding region 243 while adjusting the input value or the location of the slider.

Figure 10:
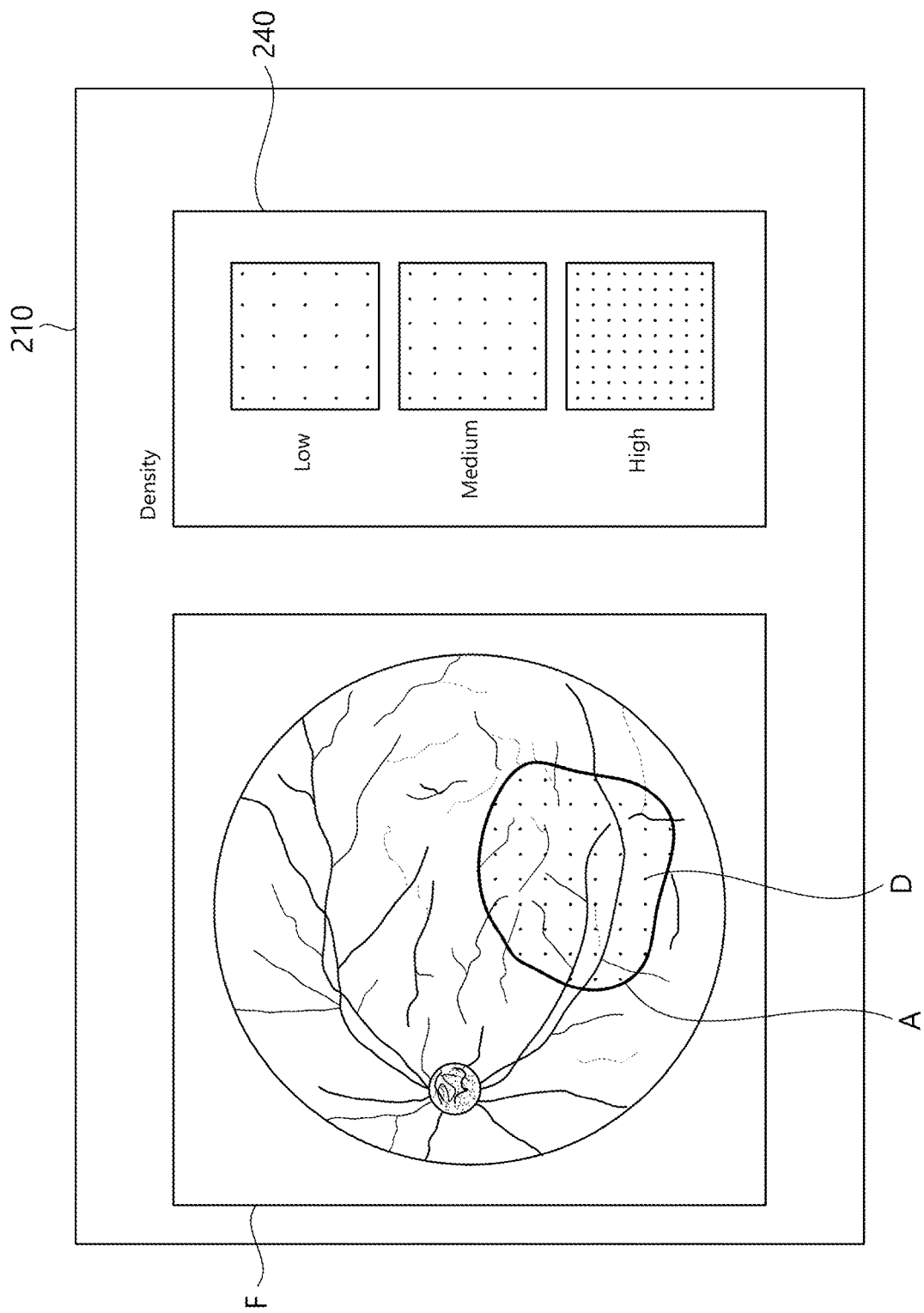
FIG. 10 is a diagram illustrating an image of a display unit to which the radiation density setting unit of FIG. 6 is applied.

FIG. 10 is a diagram illustrating an image of a display unit to which the radiation density setting unit of FIG. 6 is applied. If the user sets the radiation density of the treatment beam by the above-described radiation density setting unit 240, the set density information is displayed through the display unit 210. Here, the set radiation density information is displayed in an overlapping manner inside the treatment region that is superposed and displayed on the eyeground image of the display unit 210. The density information displayed in art overlapping manner may be displayed in the form of an option selected by the user in the radiation density setting unit 240. In FIG. 6, the dot pattern of the medium radiation density selected by the user fills the treatment region. However, a form displayed in the radiation density setting unit needs wot be the same as a form displayed on the eyeground image in an overlapping manner. Even if the option of the dot-pattern form is selected, the display may be performed using other ways corresponding to an associated radiation density, e.g., colors, shades, patterns or the like.

Figure 11:
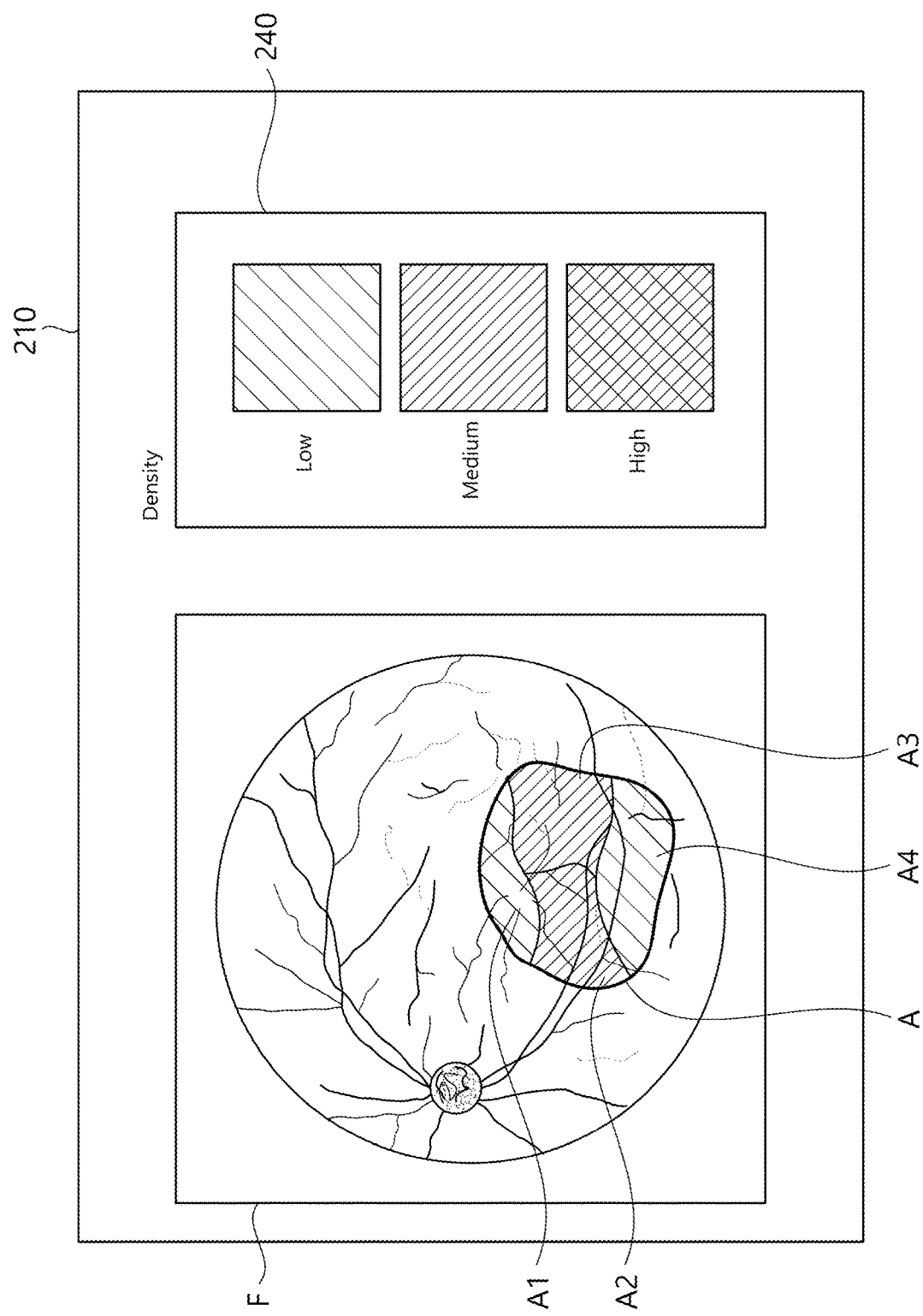
FIG. 11 is a diagram illustrating an image of a display unit to which a radiation density setting unit in accordance with another embodiment is applied.

FIG. 11 is a diagram illustrating an image of a display unit to which a radiation density setting unit in accordance with another embodiment is applied. In the embodiment of FIGS. 4 and 10, it is premised that the radiation density is set for the entire treatment region and the entire treatment region is treated in the same manner, but different treatment contents may be required even in one treatment region, depending on the progress of the lesion, the proximity to main organs such as a macula, a direction in which the lesion progresses, etc. Therefore, in an alternative embodiment shown in FIG. 11, after the treatment region setting unit 230 sets the treatment region, the treatment region may be further partitioned into a plurality of sub-regions A1 to A4 in consideration of the foregoing. Similarly to the treatment region A, the plurality of partitioned sub-regions A1 to A4 is displayed on the eyeground image of the display unit in an overlapping manner.

Meanwhile, as shown in FIG. 11, the radiation density setting unit 240 may provide the radiation density option to the user using different patterns, and the user may set the radiation density for each of the plurality of sub-regions. FIG. 11 shows a state in which the low radiation density is selected for two sub-regions A1 and A4, and the medium radiation density and the high radiation density are selected, respectively, for the remaining sub-regions A2 and A3. The radiation density information that is set as such may also be displayed on the eyeground image F of the display unit in an overlapping manner.

Figure 12:
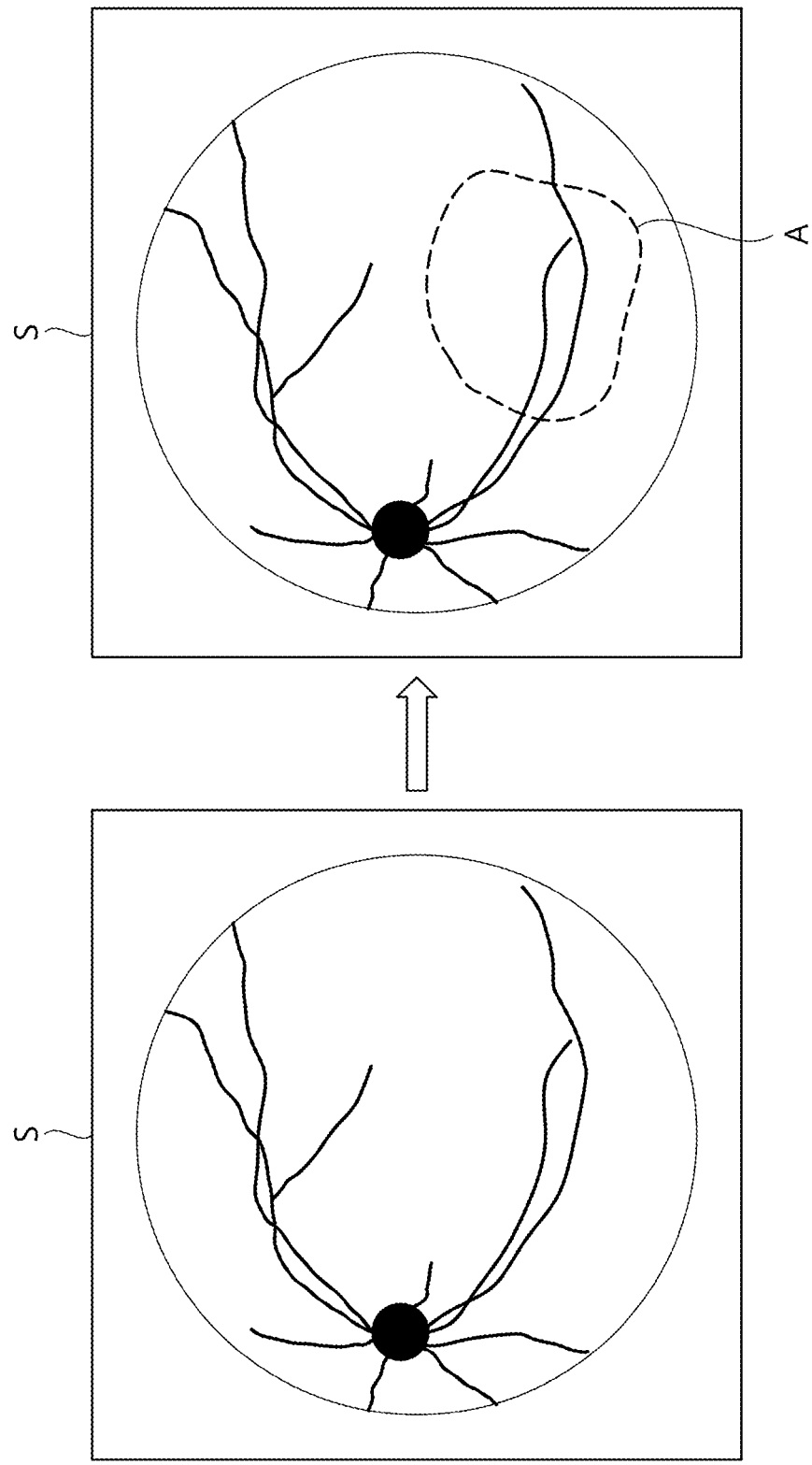
FIGS. 12 and 13 are diagrams illustrating a method of setting a treatment region and a radiation density in accordance with another embodiment.
Figure 13:
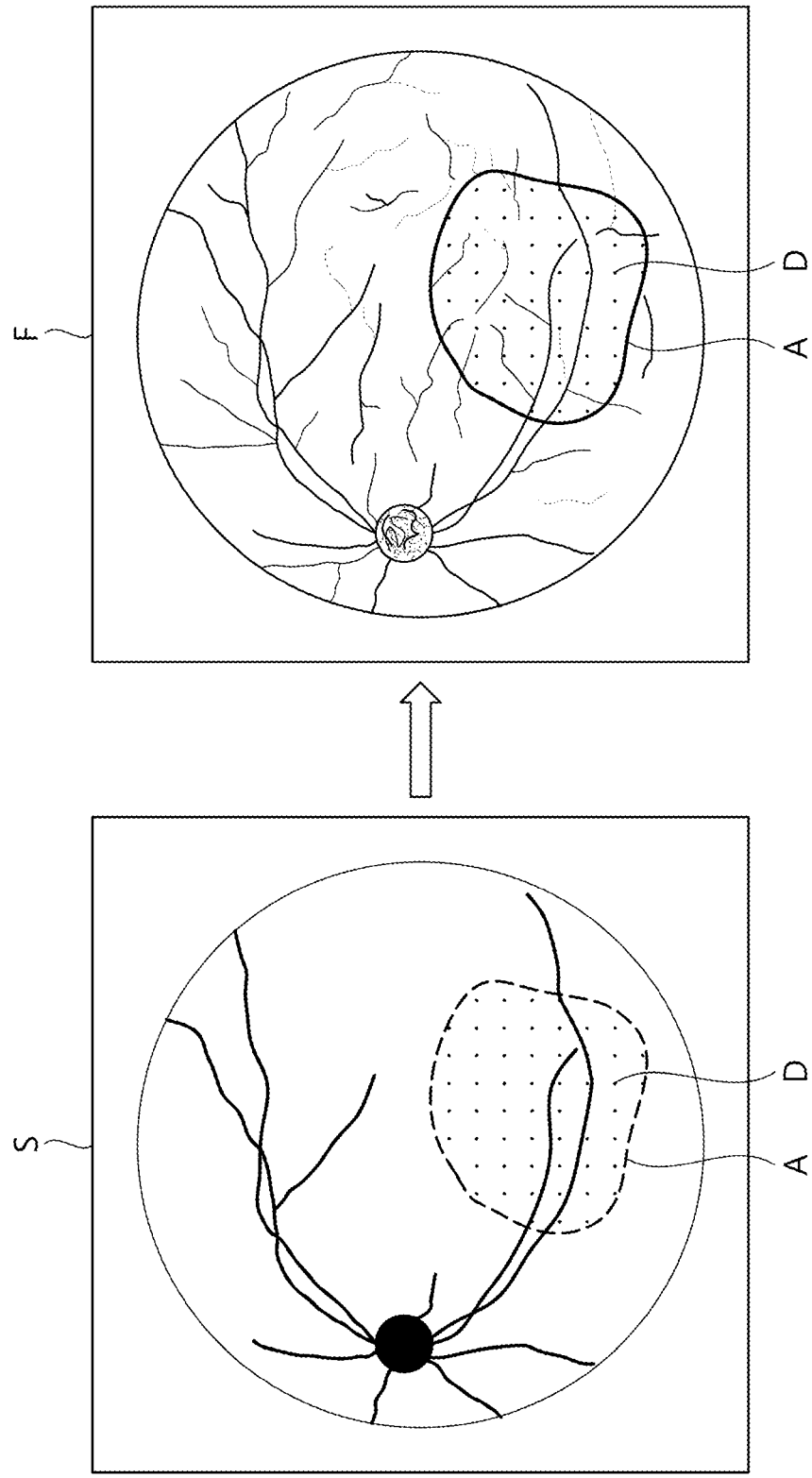

FIGS. 12 and 13 are diagrams illustrating a method of setting a treatment region and a radiation density in accordance with another embodiment. In the above-described embodiment, the treatment region setting unit directly sets the treatment region on the eyeground image displayed on the display unit. However, since the eyeground image complicatedly indicates various organs of the eyeground, it is not easy to identify the main organs of the eyeground. In addition, when the treatment region boundary or the density information is displayed in an overlapping manner in a corresponding region, it may be difficult to identify the treatment region boundary or the density information. Therefore, according to an alternative embodiment, a treatment region may be set on an eyeground sample chart S using the separate eyeground sample chart S for setting the treatment region.

As shown in FIG. 12, the eyeground sample chart S schematically displays the main organs (e.g., the location of the macula, the locations of main blood vessels, etc.) of the eyeground. Therefore, since the user sets the treatment region A on the eyeground sample chart displayed on the display unit, it is possible to design the treatment region at an accurate location in consideration of the locations of the main organs which are to be considered when designing treatment. Here, the eyeground sample chart S may be generated to display the location information of the main organ according to a patient while reflecting the eyeground information on the eyeground image acquired by the first image unit 150. Alternatively, it is also possible to configure the eyeground sample chart using a pre-stored design without reflecting the information about the patient's eyeground.

If the treatment region is set on the eyeground sample chart S through the above-described steps, the user may select and set the radiation density, based on the eyeground sample chart on which the treatment region is displayed. The set radiation density information may be displayed on the eyeground sample chart in an overlapping manner as shown in the left side of FIG. 13. Moreover, if the treatment region and the radiation density are set on the eyeground sample chart S, they may be converted as shown in the right side of FIG. 13 to be displayed to the user in the form of the eyeground image. At this time, the image processing unit 330 may display on different screens the set information in the manner of displaying the treatment region and the radiation density information, displayed on the eyeground sample chart S, on a coordinate on the eyeground image F, through image processing.

Meanwhile, in this embodiment, both the treatment-region setting and the radiation-density setting are performed on the eyeground sample chart. However, only the step of setting the radiation density may be performed on the eyeground sample chart. To be more specific, if the treatment region is set on the eyeground image, the image processing unit may process the image to generate and display the eyeground sample chart on which the treatment region is indicated, and may perform the step of setting the radiation density using the eyeground sample chart. In addition, it should be noted that the above-described eyeground sample chart may be utilized in various steps.

Figure 14:
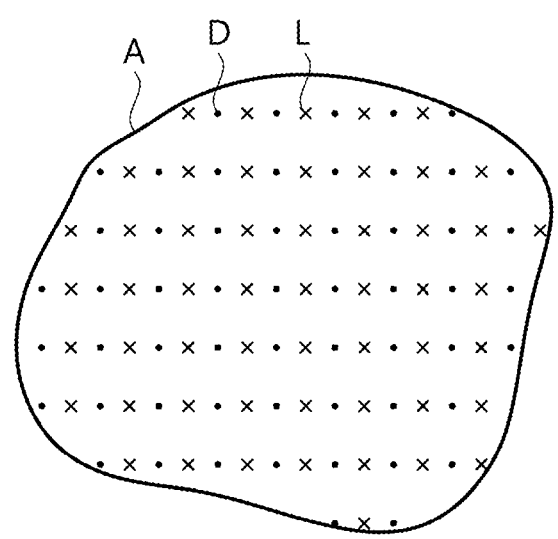
FIG. 14 is a diagram locations of treatment beams radiated onto the treatment region.

Meanwhile, if the treatment region and the radiation density are set through the above-described step, the control unit 310 operates the treatment beam radiating unit 110 based on the set information to radiate the treatment beam. FIG. 14 is a diagram locations of treatment beams radiated onto the treatment region. FIG. 14 shows dots for displaying the radiation density in the treatment region and treatment locations at which the treatment beams are substantially radiated to the eyeground.

As shown in FIG. 14, the treatment locations L at which the treatment beams are substantially radiated to the eyeground are distributed at the set radiation density in the set treatment region. However, the dots D displayed on the eyeground image in an overlapping manner may be different from the treatment locations. The reason is because the dots D for displaying the radiation density are not for the purpose of precisely indicating the locations where the treatment beams are radiated, but merely indicate the distribution shape of the treatment beams. When the radiation-density information is substantially displayed on the eyeground image in the shape of dots, the whole dot pattern D of a corresponding radiation density overlaps with the eyeground image F, and then only the dots included in the treatment region A are displayed. On the other hand, since the coordinates of the treatment locations at which the treatment beams are substantially radiated are set on the basis of the boundary of the set treatment region, the location of the dot displayed on the eyeground image may be different from the treatment location.

Meanwhile, although FIG. 14 shows that the treatment locations L to which the treatment beams are radiated are arranged in the same manner as the dot patterns D indicating the radiation density, according to an alternative embodiment, the radiating locations of the treatment beams may be configured such that the treatment beams are randomly radiated in an irregular pattern. When the treatment beams are sequentially radiated according to the order of arrangement as shown in FIG. 14, treatment may be performed again at an adjacent location before energy transmitted by the treatment beam that is previously radiated is sufficiently dispersed, so that energy overlapping may occur, thus causing damage to the tissue. Therefore, as an alternative embodiment, it is also possible to control the treatment beam radiating unit such that the treatment beam is radiated into the treatment region at the number of times corresponding to the set radiation density, and is randomly radiated in an irregular manner rather than in an aligned location.

Figure 15:
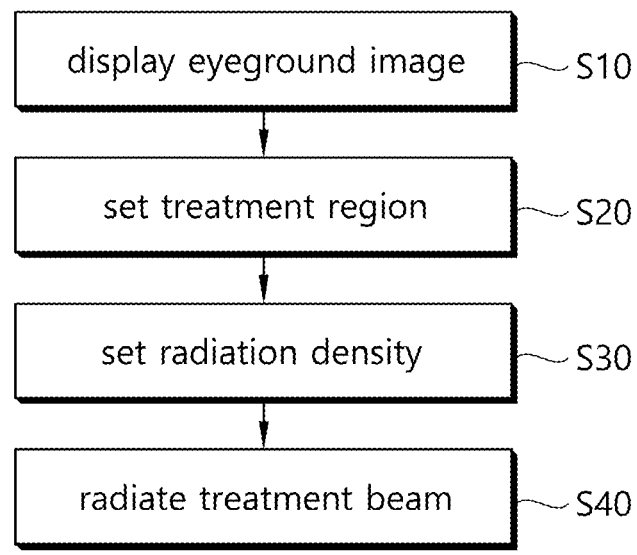
FIG. 15 is a flowchart illustrating a method of controlling the ophthalmic treatment apparatus of FIG. 1.

Hereinafter, the control method of the above-described ophthalmic treatment apparatus and the treatment method using the same will be described in detail with reference to FIG. 15. FIG. 15 is a flowchart illustrating the method of controlling the ophthalmic treatment apparatus of FIG. 1. Hereinafter, according to an embodiment, an example where the selective retina therapy is performed will be mainly described, and important steps of the method of controlling the device will be mainly described for the convenience of description.

As shown in FIG. 12, the control method includes a step S10 of displaying an eyeground image, a step S20 of setting a treatment region, a step S30 of setting a radiation density, anti a step S40 of radiating a treatment beam.

The eyeground-image displaying step S10 is a step of displaying a two-dimensional eyeground image acquired through the first image unit 150 on the display unit 210 of the interface unit 20. The user may diagnose the patient's lesion based on the eyeground image displayed through the display unit 210 and then design the treatment.

The user performs the step of setting the region where treatment is performed using the displayed eyeground image F (S20). This step may be performed by drawing the boundary of the treatment region on the eyeground image using a touch screen or a separate input device. The set treatment region may be displayed on the eyeground image F of the display unit in an overlapping manner. Here, as described above, the set treatment region A may be further divided into a plurality of sub-regions A1 to A4 in consideration of the progress of the lesion, the positional relationship with adjacent organs, etc. Further, the treatment region may be set on a separate eyeground sample chart S instead of the eyeground image F.

If the treatment region is set, the step of setting the radiation density of the treatment beam radiated to the treatment region is performed (S30). The radiation density may be set by the user through the radiation density setting unit 240 displayed on the display unit, and the set radiation-density information may be displayed on the eyeground image of the display unit (or the eyeground sample chart) in an overlapping manner. Here, the displayed radiation-density information may use various forms, such as the density, color, shade, pattern, or value of the dot pattern. Further, when the treatment region is divided into a plurality of sub-regions, the radiation density may be individually set for each sub-region.

If the treatment region and the radiation density are set in this manner, the step of radiating the treatment beam is performed (S40). The control unit controls the treatment beam radiating unit to radiate the treatment beam into the treatment region at the number of times corresponding to the set radiation density. According to this embodiment, in the case of performing the selective retina therapy, the control unit 310 radiates a plurality of micropulses that are sequentially increased in intensity to a first location, and stops radiating the pulse when the targeted state change is detected through the monitoring unit 140. Further, after the treatment location is changed into a second location, the treatment beam is radiated in the same manner as the first location. At this time, the treatment beam radiated to the treatment region may be radiated at a location different from the dot pattern displayed on the eyeground image, and the treatment beam may be radiated in a state where a location is changed in a random manner.

Hereinbefore, the ophthalmic treatment apparatus and the control method thereof, capable of performing the optimal treatment according to a patient's condition by setting the treatment region and the radiation density have been described. Although the aforementioned embodiment mainly describes the selective retina therapy using the second light source, the present disclosure may also be applied to the retina photocoagulation using the first light source without being limited thereto.

Furthermore, although the embodiment using the eyeground image and the eyeground tomographic image acquired by the first and second image units has been described, the present disclosure may use an eyeground image and an eyeground tomographic image acquired by a separate photographing device or diagnostic device without being limited thereto.

Although the present disclosure was described in detail with reference to specific embodiments, the present disclosure is not limited to these embodiments. It is apparent to those skilled in the art that the present disclosure may be changed and modified in various ways without departing from the scope of the present disclosure, which is described in the following claims.

The invention claimed is:

1. An ophthalmic treatment apparatus comprising:
 a display unit for displaying an image of a patient's eyeground;
 a treatment region setting unit for setting a treatment region on the basis of the image of the patient's eyeground;
 a treatment beam radiating unit for radiating a treatment beam to the set treatment region;
 a radiation density setting unit for setting radiation density of the treatment beam radiated to the set treatment region; and
 a control unit for controlling the treatment beam radiating unit so as to radiate the treatment beam onto the set treatment region on the basis of the set density,
 wherein the display unit displays an eyeground sample chart in which main organs of the eyeground are schematically displayed, and the treatment region setting unit sets the treatment region on the eyeground sample chart.

2. The ophthalmic treatment apparatus of claim 1, wherein the set treatment region is displayed in an overlapping manner on an eyeground image displayed on the display unit.

3. The ophthalmic treatment apparatus of claim 2, wherein information about the set radiation density is displayed in an overlapping manner on the eyeground image displayed on the display unit.

4. The ophthalmic treatment apparatus of claim 3, wherein the information about the set radiation density displayed on the display unit is displayed using at least any one of a dot pattern distributed at a set density, a color, a shade, a pattern, or a value.

5. The ophthalmic treatment apparatus of claim 1, wherein the radiation density setting unit provides a plurality of options corresponding to various radiation densities to a user through the display unit.

6. The ophthalmic treatment apparatus of claim 5, wherein the plurality of options is provided using at least one of a plurality of dot patterns distributed at different densities, a plurality of different colors, shades or patterns, and different values.

7. The ophthalmic treatment apparatus of claim 1, wherein the radiation density setting unit is configured so that the user may directly input a radiation density value, and displays a distribution shape corresponding to the input radiation density value to the user.

8. The ophthalmic treatment apparatus of claim 1, wherein the radiation density setting unit sets the information about the set radiation density in the treatment region displayed on the eyeground sample chart.

9. The ophthalmic treatment apparatus of claim 1, wherein the treatment region setting unit is configured to set the set treatment region into a plurality of sub-regions according to a patient's eyeground condition, and
 wherein the radiation density setting unit is configured to set the radiation density of the treatment beam for each of the plurality of sub-regions.

10. The ophthalmic treatment apparatus of claim 1, wherein the treatment beam radiating unit randomly radiates the treatment beam to the set treatment region at the set radiation density.

11. A method of controlling an ophthalmic treatment apparatus, the method comprising:

displaying an eyeground image on a display unit;
setting a treatment region in which treatment is performed, on the basis of the eyeground image;
setting radiation density of treatment beam radiated to the treatment region; and
radiating the treatment beam to the set treatment region at the set radiation density,
wherein, in the setting the treatment region, an eyeground sample chart in which main organs of the eyeground are schematically displayed is displayed on the display unit, and the user sets the treatment region on the eyeground sample chart.

12. The method of claim 11, wherein, in the setting the treatment region, a boundary of the treatment region is displayed on the eyeground image displayed on the display unit to set the treatment region, and the display unit displays the set treatment region on the eyeground image in an overlapping manner.

13. The method of claim 12, wherein the setting the radiation density further comprises:
displaying information about the set radiation density inside the treatment region displayed on the eyeground image in an overlapping manner.

14. The method of claim 11, wherein, in the setting the radiation density, a plurality of options corresponding to various radiation densities is displayed through the display unit, and a user sets the radiation density by selecting one of the plurality of options, and
wherein the plurality of options is provided using at least one of a plurality of dot patterns distributed at different densities, a plurality of different colors, shades or patterns, and different values.

15. The method of claim 11, wherein, in the setting the radiation density, the user directly inputs a radiation density value, and a distribution shape of the treatment beam corresponding to the input radiation density value is provided to the user.

16. The method of claim 11, wherein the information about the set radiation density is displayed in the treatment region displayed on the eyeground sample chart.

17. The method of claim 11, wherein the setting the treatment region further comprises partitioning the set treatment region into a plurality of sub-regions according to a patient's eyeground condition, and
wherein, in the setting the radiation density, the radiation density of the treatment beam is set for each of the partitioned sub-regions.

18. The method of claim 11, wherein, in radiating the treatment beam, the treatment beam is randomly radiated to the set treatment region at the set radiation density.

19. A treatment method using an ophthalmic treatment apparatus, the method comprising:
displaying an eyeground image on a display unit;
setting a treatment region in which treatment is performed, on the basis of the eyeground image;
setting radiation density of treatment beam radiated to the treatment region; and
radiating the treatment beam to the set treatment region at the set radiation density,
wherein, in the setting the treatment region, an eyeground sample chart in which main organs of the eyeground are schematically displayed is displayed on the display unit, and the user sets the treatment region on the eyeground sample chart.

* * * * *